United States Patent [19]

Auschner et al.

[11] Patent Number: 4,596,895

[45] Date of Patent: Jun. 24, 1986

[54] PROCESS FOR THE CATALYTIC PREPARATION OF ALKALI ALCOHOLATES

[75] Inventors: Reinhard Auschner, Troisdorf; Peter Schmittinger, Niederkassel; Rüolf Stephan, Troisdorf-Sieglar, all of Fed. Rep. of Germany

[73] Assignee: Dynamit Nobel AG, Troisdorf, Fed. Rep. of Germany

[21] Appl. No.: 785,159

[22] Filed: Oct. 7, 1985

[30] Foreign Application Priority Data

Oct. 10, 1984 [DE] Fed. Rep. of Germany ....... 3437152

[51] Int. Cl.$^4$ ............................................. C07C 29/70
[52] U.S. Cl. .................... 568/851; 252/182; 252/185
[58] Field of Search ........................................ 568/851

[56] References Cited

U.S. PATENT DOCUMENTS

| | | | |
|---|---|---|---|
| 2,000,329 | 5/1935 | Heisel et al. | 568/851 |
| 2,069,403 | 2/1937 | Cunningham | 568/851 |
| 2,069,404 | 2/1937 | Cunningham | 568/851 |
| 2,287,088 | 6/1942 | Cohen | 568/851 |
| 2,437,272 | 3/1948 | Robinson | 568/851 |
| 2,570,058 | 10/1951 | Hunter | 568/851 |
| 2,732,284 | 1/1956 | Sukowski | 568/851 |
| 2,761,880 | 9/1956 | Gerber et al. | 568/851 |
| 3,716,567 | 2/1973 | Termin et al. | 568/851 |

FOREIGN PATENT DOCUMENTS

| | | | |
|---|---|---|---|
| 477198 | 9/1951 | Canada | 568/851 |
| 28963 | 7/1972 | Japan | 568/851 |
| 403921 | 1/1934 | United Kingdom | 568/851 |
| 490387 | 8/1938 | United Kingdom | 568/851 |

*Primary Examiner*—J. E. Evans
*Attorney, Agent, or Firm*—Felfe & Lynch

[57] ABSTRACT

A process is described for the catalytic preparation of alkali alcoholates from alkali amalgams and alcohols. The catalyst is lump anthracite having a surface treated to have a heavy metal oxide or mixtures of heavy metal oxides. Preferably a mixture of nickel oxide and molybdenum oxide is used. Aliphatic alcohols with 1 to 4 carbon atoms are preferred as the alcohol component.

5 Claims, No Drawings

PROCESS FOR THE CATALYTIC PREPARATION OF ALKALI ALCOHOLATES

THE BACKGROUND OF THE INVENTION

The present invention is in a process for the catalytic preparation of alkali alcoholates from alkali amalgams and alcohols.

Alkali alcoholates, especially those whose alcohol component contains up to 4 carbon atoms, are valuable chemicals. They are used, for example, as catalysts in the synthesis of many organic compounds. The alcoholates of sodium and potassium have acquired particular practical importance. Several methods are known for the preparation of alkali alcoholates (F. A. Dickes, Ber. Dtsch. Chem. Ges. 63, 2753 [1930]). Thus, solutions of alkali hydroxides in an alcohol contain alkali alcoholates in equilibrium. By removing the water that is in this equilibrium, by distillation for example, pure alkali alcoholates are obtained. Especially in the case of low-boiling alcohols, however, a great deal of energy is needed for this kind of equilibrium alteration.

Pure alkali alcoholates are arrived at directly by dissolving an alkali metal in the corresponding alcohol. Sodium and potassium react vigorously with low aliphatic alcohols, such as methanol and ethanol, with the evolution of hydrogen. Higher alcohols, such as the propanols and butanols, are reacted with alkali metals preferably above the melting point of the latter, with stirring and under pressure if required. The method of direct preparation of the alkali alcoholates from metal and alcohol scarcely qualifies as a commercial process, because the alkali metals required as the starting materials are too expensive.

It is more economical to use as the alkali source the liquid alkali amalgam that is produced in the electrolysis of chlorinated alkali by the mercury method.

The reaction of alkali amalgam with alcohols and the use of catalysts for this reaction are known. R. B. MacMullin, in Chemical Engineering Progress, September 1950, p. 440, mentions, among other things, the reaction of alkali amalgam with methanol in a reactor which contains graphite as catalyst. In U.S. Pat. Nos. 2,336,045 and 2,761,880, nonamalgamating substances, such as iron, graphite or mixtures thereof, are proposed as catalysts. In U.S. Pat. No. 2,069,403, metal meshes made of heavy metal alloys are described as catalysts.

The problem was to find a process that satisfies the following requirements.

The reaction between the amalgam and the alcohol should take place at the highest possible rate in order to achieve high volume-time yields in a technical reactor. Furthermore, after this reaction the concentration of the alkali metal in the amalgam should be as low as possible, since the residual content of alkali metal has to be reacted with water in a second reaction to form alkali hydroxide solution, which is not a target product of the present process. This reaction of the amalgam with water is necessary in order to completely react the alkali metal contained in the amalgam. Otherwise, when the mercury is recycled into the electrolysis cell the alkali metal concentration would become too high and the amalgam would become solid. The process should be performable in a continuous manner. In a technical decomposer with a bed of a known catalyst of 1 m height, and 0.2 to 0.35 wt.-% of sodium or potassium in the mercury at the inlet, the residual content of alkali metal in the amalgam at the outlet will be between 50 and 70% of the inlet concentration.

THE INVENTION

It has been found that the decomposition of alkali amalgam by alcohols is surprisingly catalyzed especially well by heavy metal oxides and mixtures thereof, which are finely distributed on the surface of anthracite. In this case the anthracite has the advantage over the previously described graphite of better wetting by the liquid reactants amalgam and alcohol. In a continuous reactor, in which the reactants are to come into contact on catalyst on the basis of the countercurrent principle as finely divided as possible, the wetting of the catalyst is important, since in the present case it is a question of a reaction between two liquid phases and one solid phase. The residual content of alkali metal in the amalgam according to the invention is reduced to between 5 and 30% of the inlet concentration.

Furthermore, anthracite is highly resistant to attrition. Its catalytic action is substantially increased by applying oxides or oxide mixtures of heavy metals to its surface. Thus, in comparison to the known use of heavy metals and their alloys as catalysts in the form of sheets, meshes or chips, a large surface of catalytically active substance is achieved in this manner, while only small amounts of the catalyst material are needed, since only the surface of the anthracite support material is occupied by the metal oxides. Useful oxides are the oxides of nickel, molybdenum, iron, manganese or cobalt.

An especially high catalytic activity is obtained when a mixture of the oxides of nickel and molybdenum is used.

According to the invention, it is preferably aliphatic alcohols of 1 to 4 carbon atoms that are reacted in the process. However, other alcohols can also be used as starting material in this process, such as, for example, aliphatic alcohols with more than 4 carbon atoms.

EXAMPLES

Example 1 (Preparation of the catalyst)

50 kg of nickel (II) acetate tetrahydrate and 10 kg of sodium molybdate dihydrate are dissolved in 500 l of water at 95° C. 500 kg of nut anthracite, loose, in a size of 5 to 30 mm, is placed in this hot, saturated solution, and allowed to cool down to 20° C. for about 24 hours. The solution is drawn off, the impregnated material is dried, and is heated in an oven, such as a muffle oven or tunnel oven, to 400° to 1200° C. Then the material is allowed to cool and the fines (grain size under 4 mm) are sifted out.

In this treatment the following processes take place:

Metal salt deposits itself on the hard support material by precipitating from the hot-saturated metal salt solution as it cools again, and this salt converts at temperatures of 400° to 1200° C. to the corresponding metal oxides, sinters, and after sintering adheres firmly to the support material.

Examples 2 to 5

In order to judge the activity of the catalyst samples, 100 g of sodium amalgam containing 0.3 wt.-% of sodium was placed in a model reactor and 10 g of catalyst grains in the same size as in Example 1 were added. Over this 100 ml of methanol was poured. Both the amalgam and the alcohol were simultaneously stirred with the same stirrer. The increase of the conductivity of the alcoholic alcoholate solution that formed at 60° C. serves as a measure of the activity.

The following time periods required for the complete decomposition of the amalgam were found in this model reactor:

| Example | Catalyst | Reaction with methanol (in minutes) |
| --- | --- | --- |
| 2 | Decomposer graphite | 57.5 ± 3 |
| 3 | Nut anthracite, untreated | 44.3 ± 3 |
| 4 | Nut anthracite activated with nickel (II) oxide | 18.5 ± 1 |
| 5 | Nut anthracite activated with a mixture of nickel (II) oxide and molybdenum (VI) oxide | 5.5 ± 0.3 |

The best decomposition performance is found with the catalyst prepared as described above, in Example 5.

Examples 6 to 9

In additional series of experiments, the reaction times with longer-chain alcohols were determined in a manner similar to Examples 2 to 5.

In comparison to Examples 2 to 5, the reaction times are lengthened:

| | |
| --- | --- |
| Using ethanol | by a factor of 2 (Example 6) |
| Using 1-propanol | by a factor of 5 (Example 7) |
| Using 1-butanol | by a factor of 14 (Example 8). |

Secondary alcohols react decidedly more poorly; for example, in the case of the reaction of 2-butanol, the reaction time is lengthened by a factor of 23 (Example 9).

It will be understood that the specification and examples are illustrative but not limitative of the present invention and that other embodiments within the spirit and scope of the invention will suggest themselves to those skilled in the art.

We claim:

1. A process for the catalytic preparation of alkali alcoholates from alkali amalgams and alcohols, comprising reacting the alkali amalgam and alcohol in the presence of a catalyst of lump anthracite as support material, said catalyst having a heavy metal oxide or heavy metal oxide mixtures adhering to its surface.

2. The process according to claim 1, wherein the heavy metal oxide mixture is a mixture of nickel oxide and molybdenum oxide.

3. The process according to claim 1, wherein the alcohol is an aliphatic alcohol having 1 to 4 carbon atoms.

4. The process of claim 1, wherein the alkali amalgam is sodium or potassium amalgam.

5. The process of claim 1, wherein the heavy metal oxide or heavy metal oxide mixture is deposited from solution on to the lump anthracite surface.

* * * * *